(12) United States Patent
Ng et al.

(10) Patent No.: US 10,874,342 B2
(45) Date of Patent: Dec. 29, 2020

(54) BRAIN INJURY MONITORING SYSTEM

(71) Applicant: L3 Applied Technologies, Inc., San Diego, CA (US)

(72) Inventors: Laurel Jean Ng, San Diego, CA (US); Vladislav Volman, San Diego, CA (US); Mark Adkins, San Diego, CA (US)

(73) Assignee: L3 APPLIED TECHNOLOGIES, INC., San Diego, CA (US)

( * ) Notice: Subject to any disclaimer, the term of this patent is extended or adjusted under 35 U.S.C. 154(b) by 353 days.

(21) Appl. No.: 15/961,845

(22) Filed: Apr. 24, 2018

(65) Prior Publication Data

US 2019/0320965 A1    Oct. 24, 2019

(51) Int. Cl.
*A61B 5/00* (2006.01)
*A61B 5/11* (2006.01)

(52) U.S. Cl.
CPC .......... *A61B 5/4064* (2013.01); *A61B 5/6803* (2013.01); *A61B 5/7282* (2013.01); *A61B 5/11* (2013.01); *A61B 5/7235* (2013.01); *A61B 5/746* (2013.01); *A61B 2503/10* (2013.01); *A61B 2562/0219* (2013.01)

(58) Field of Classification Search
CPC .......... A61B 5/7235; A61B 2562/0219; A61B 5/6803; A61B 5/7275; A61B 5/4064; A61B 5/7282; A61B 5/11; A61B 5/746; A61B 2503/10
See application file for complete search history.

(56) References Cited

U.S. PATENT DOCUMENTS

| 2010/0222694 | A1* | 9/2010 | Causevic | A61B 5/048 600/544 |
| 2011/0184663 | A1* | 7/2011 | Mack | G01L 1/26 702/41 |
| 2014/0266752 | A1* | 9/2014 | John | G08B 21/0461 340/665 |
| 2016/0296153 | A1* | 10/2016 | Lovoi | A61B 5/7282 |

OTHER PUBLICATIONS

International Search Report and Written Opinion for International Patent Application No. PCT/US2019/026856 dated Jul. 2, 2019, 8 pages.

* cited by examiner

*Primary Examiner* — Christine H Matthews
*Assistant Examiner* — Joshua Daryl D Lannu
(74) *Attorney, Agent, or Firm* — Loza & Loza, LLP; Anthony G. Smyth

(57) ABSTRACT

Systems, methods, and apparatus are described that employ a fast concussion model usable to detect occurrence of traumatic events that can contribute to mild traumatic brain injury (mTBI) and to assess the risk that mTBI has occurred or is likely to occur should further traumatic events occur. A method includes receiving motion data related to a head acceleration event from sensors configured to detect head motion of a subject, using the motion data to obtain an estimate of axon signal dysfunction affecting a component of the subject's brain as a result of the head acceleration event, determining a Neurologic Injury Measure (NIM) from the estimate of axon signal dysfunction, and generating a probability that the subject has been concussed by the head acceleration event based on the NIM. The estimate of axon signal dysfunction may be based on strain at nodes of Ranvier in the component of the subject's brain.

22 Claims, 12 Drawing Sheets

BRAIN INJURY MONITORING SYSTEM

TECHNICAL FIELD

The present disclosure relates generally to assessment of concussion after traumatic impacts, and more particularly, to a distributed approach to evaluating and characterizing the concussive effect of traumatic impact events detected by wearable sensors.

BACKGROUND

Mild traumatic brain injury (mTBI) resulting from concussion is a frequently-occurring type of brain trauma. In many instances, concussions produce a disturbance of brain function rather than structural injury. Accordingly, persons affected by mTBI often demonstrate no immediate post-trauma abnormalities. Concussive trauma may nevertheless result in mechanical injury to the axonal component that can result in acute to long-term damage and axonal degeneration. Conventional models for mTBI are complex and require significant contextual and subject-specific information. These conventional models are difficult to deploy for use in the field, whether for occupational health hazards including trauma-inducing events occurring during sporting events or combat.

There exists a need for improvements in protocols and methods for detecting, predicting and preventing mTBI that can be deployed in fields of activity that produce traumatic impacts, blast exposure and/or other traumatic events to the head.

SUMMARY

Certain aspects of the disclosure relate to systems, apparatus, methods and techniques for implementing, maintaining and managing a local, fast concussion model usable to detect occurrence of traumatic events that can contribute to mTBI and to assess the risk that mTBI has occurred or is likely to occur should further traumatic events occur.

In various aspects of the disclosure, a method performed by a portable communication device includes receiving motion data related to an extraordinary head acceleration event from a plurality of sensors configured to detect head motion of a subject, using the motion data to obtain an estimate of axon signal dysfunction affecting one or more components of the subject's brain as a result of the head acceleration event, determining a Neurologic Injury Measure (NIM) from the estimate of axon signal dysfunction, and generating a probability that the subject has been concussed by the head acceleration event based on the NIM.

In some aspects, the estimate of axon signal dysfunction is obtained by determining strain at nodes of Ranvier in the one or more components of the subject's brain, and estimating axon signal dysfunction by translating the strain at the nodes of Ranvier to functional decrement of axon signaling. Determining the strain at the nodes of Ranvier may include determining strain at nodes of Ranvier in the subject's corpus callosum.

In some aspects, the NIM may be determined using a volume-weighted average of axon signal dysfunction over a plurality of axons in the one or more components of the subject's brain. The plurality of axons may be located in the corpus callosum of the subject's brain.

In one aspect, the head acceleration event results from an impact to the subject's head or exposure of the subject's head to a blast. In another aspect, the head acceleration event results from an application of an accelerative load to the subject's body.

In certain aspects, the motion data may be transformed to obtain head kinematics abstracted from the placement of the plurality of sensors with respect to the subject's head. At least one sensor may be mechanically decoupled from the subject's head, such that the sensor is unattached to the subject's head. One or more sensor may provide a stream of image data that captures movement of the subject's head.

In some aspects, a probability that the subject has been concussed may be determined using dose-response information obtained from a mechanistic concussion model. The dose-response information may characterize a cumulative effect of multiple extraordinary head acceleration events affecting the subject's head. The NIM may be correlated to an injury outcome using dose-response information obtained from a mechanistic concussion model. The NIM may be correlated to the injury outcome using a fast concussion model comprising a plurality of transforms received from a network server that maintains a mechanistic concussion model.

In certain aspects, the motion data related to the extraordinary head acceleration event may be transmitted to the network server that maintains the mechanistic concussion model. Information obtained from a plurality of extraordinary head acceleration events affecting one or more subjects may be used to update the fast concussion model. One or more updated transforms may be received from the network server that maintains the mechanistic concussion model after the fast concussion model is updated. Visualization data may be received from the network server that maintains the mechanistic concussion model. A visualization of the extraordinary head acceleration event may be provided on the portable communication device.

In some aspects, the plurality of sensors may be configured based on format and timing requirements defined for an interface that transforms the motion data. Visualization data may be generated using the motion data related to the extraordinary head acceleration event and based on configuration of the plurality of sensors. A visualization of the extraordinary head acceleration event may be displayed or provided using the portable communication device.

In one aspect, a wireless communication protocol may be used for periodically communicating with the plurality of sensors. The motion data related to the extraordinary head acceleration event may be received during one or more periodic communication events.

In one aspect, the motion data related to the extraordinary head acceleration event may be received while communicating with the plurality of sensors responsive to an indication that the extraordinary head acceleration event has occurred.

In one aspect, the user of the portable communication device may be alerted when the probability that the subject has been concussed by the extraordinary head acceleration event exceeds a configured threshold.

In various aspects of the disclosure, an apparatus has a communication interface adapted to couple the apparatus to a plurality of wearable sensors, and a storage medium configured with transforms generated from a mechanistic model of head kinematics, and a processing circuit. The processing circuit may be configured to receive motion data related to an extraordinary head acceleration event from a plurality of sensors configured to detect head motion of a subject, determine strain at nodes of Ranvier in one or more components of the subject's brain resulting from the head acceleration event, estimate axon signal dysfunction affecting the one or more components of the subject's brain by translating the strain at the nodes of Ranvier to functional decrement of axon signaling, determine a NIM from estimated axon signal dysfunction, and generate a probability that the subject has been concussed by the head acceleration event based on the NIM.

In various aspects of the disclosure, a processor readable storage medium is disclosed. The storage medium may be a non-transitory storage medium and may store code that, when executed by one or more processors, causes the one or more processors to receive motion data related to an extraordinary head acceleration event from a plurality of sensors configured to detect head motion of a subject, determine strain at nodes of Ranvier in one or more components of the subject's brain resulting from the head acceleration event, estimate axon signal dysfunction affecting the one or more components of the subject's brain by translating the strain at the nodes of Ranvier to functional decrement of axon signaling, determine a NIM from estimated axon signal dysfunction, and generate a probability that the subject has been concussed by the head acceleration event based on the NIM.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Several aspects will now be presented with reference to various apparatus and methods. These apparatus and methods will be described in the following detailed description and illustrated in the accompanying drawings by various blocks, modules, components, circuits, steps, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

Example of a Brain Injury Monitoring System

Certain aspects disclosed herein employ validated, predictive biomechanical, physiological, and neurological models of mTBI processes to characterize and measure the effects of traumatic impacts measured by sensors worn by a monitored subject. A system may determine a relationship between expected or observed symptoms and trauma dosage, which may express severity of an impact and/or cumulative severity of multiple impacts. In one aspect, the system may provide an analysis of the effect of one or more concussive impacts on the monitored subject, and may provide warnings and/or alarms that enable informed decision-making with respect to the monitored subject's exposure to further impact.

Figure 1:
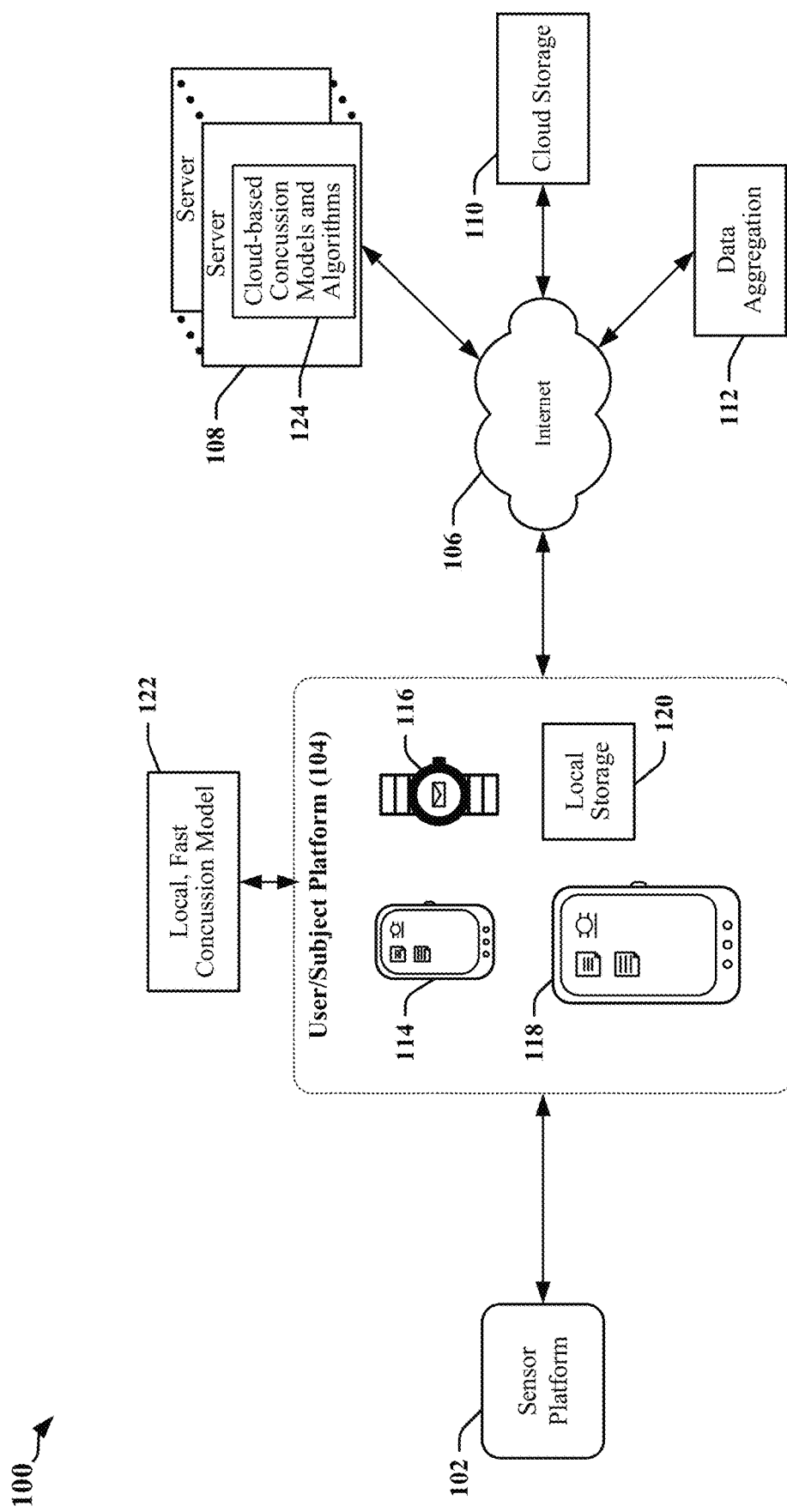
FIG. 1 illustrates an end-to-end Brain Injury Monitoring System that may be implemented in accordance with certain aspects disclosed herein.

FIG. 1 illustrates an example of an end-to-end Brain Injury Monitoring System (BIMS) 100 that may be implemented in accordance with certain aspects disclosed herein. In the example, a combination of a mobile sensor platform 102, user processing platform 104 networked server 108, and other networked resources 110, 112 may be employed to capture and analyze motion data that may be transformed or processed to represent kinematics at the center of gravity of the head of a subject. The motion data may be captured through the operation of the sensor platform 102, which may support or integrate multiple sensors, including wearable sensors. The motion data may be used to assess the risk that the subject may have experienced concussion or is at increased risk of suffering concussion from traumatic impact events. The mobile sensor platform 102 may include one or more monitoring devices used to configure, monitor and/or read wearable sensors, and one or more sensors that is physically unattached to the subject including, for example, a high-speed video camera that maintains the subject within its field of view while a traumatic event is occurring. The mobile sensor platform 102 may include a communication interface used to communicate sensor data and/or motion data derived from the sensor data to the user processing platform 104 or through an intermediary device communicatively coupled to the user processing platform 104. The mobile sensor platform 102 may be configured to acquire motion data that can be used to estimate risk of concussion. Risk of concussion may be calculated from mechanistic models that can provide a reference relating kinematics data to traumatic impacts to the head of a subject, and that can estimate expected effects of such traumatic impacts. In one example, the traumatic impacts may result from sporting activities. In another example, traumatic events may occur during combat and may result from impacts and/or blast exposure to the head and/or body of the subject. In another example, traumatic events may be an occupational hazard in certain industries.

In some examples, the user processing platform 104 may be configured with a mobile concussion model 122 that can be used to process and analyze motion data corresponding to impacts or blasts affecting the head of the subject. The user processing platform 104 may assess risk of concussion from traumatic impact events using the mobile concussion model 122. Cloud-based networked servers 108 may maintain or operate one or more instances, configurations and/or variants of a mechanistic concussion model (concussion models 124) that can be used to analyze motion data. These concussion models 124 may be updated based on motion data captured from sensors and related to multiple traumatic events affecting one or more subjects. Updates to the concussion models 124 may be made using outcome and other clinical data related to individual traumatic events, and/or series of traumatic events affecting one or more monitored subjects. The cloud-based networked servers 108 may be used to implement updated mobile concussion models 122 and/or to provide updated subject-specific information to user processing platforms 104.

The mobile sensor platform 102 may incorporate and/or adapt a variety of conventional sensors. The mobile sensor platform 102 may include a configuration of sensors optimized for collecting motion data. In some implementations, the BIMS 100 provides or supports a defined interface to permit integration of suitable sensor devices. In one example, the interface may provide an open Application Programming Interface (API) that enables sensors or sensor managers to supply motion data in a format that can be used to determine the effect of an impact, blast or other traumatic event on the head of a subject. The BIMS 100 may be configurable to analyze motion data using a model-based algorithm to estimate the risk of concussion based on the supplied head motion data. The BIMS 100 may provide a visual representation of the risk of concussion to a user through a display system of the user processing platform 104. The user may be a monitored subject, and/or a person responsible for monitoring one or more monitored subjects.

In some instances, data and concussion risk outcomes can be stored in secure, managed cloud-based storage 110 that permits the user to retrieve and visualize previous impact information, aggregated statistics while protecting personal data. Concussion information related to multiple subjects may be aggregated using a networked server 108 or data aggregator 112. A data aggregator 112 may aggregate data from multiple sources after stripping identifying information or other personal data to obtain aggregated multi-subject data that may be used to generate multi-subject baselines. In one example, a subject may view personal impact data and projections and may compare the personal impact data and projections with one or more multi-subject baselines. In the latter example, access to levels of personal and multi-subject information, analysis and projections may be provided in accordance with a user profile (type of user), subscription plan, and so on.

Concussion Models, Transforms and Algorithms

In various aspects of this disclosure, a BIMS 100 may enable a user device 114, 116, 118 to operate using one or more mobile concussion models 122. The mobile concussion models 122 may include fast, light and compact implementations of the concussion models 124 maintained by the networked servers 108. In one example, a mobile concussion model 122 deployed in a mobile device may include simplified transforms, algorithms and statistical tools that are customized for an intended application of a concussion model 124. A mobile concussion model 122 may be configurable for operation on a user device 114, 116, 118 operated by a subject or other user associated with the subject, and/or in a cloud-based processing environment. In at least some implementations, a combination of a user device 114, 116, 118 and cloud-based processing environment may be used to process motion data. In one example, the mobile concussion model 122 may be adapted or configured to provide an instant evaluation of sensor data or motion data derived from sensor data. The user device 114, 116, 118 may be a smartphone 114, smartwatch 116, tablet computer 118 or the like. Motion data and impact analysis derived from the motion data may be stored in a local memory or storage 120.

According to certain aspects, a concussion algorithm may be configurable to use the mobile concussion model 122 to calculate the effects of impacts from motion data provided by sensors external to the head of the subject and to establish or quantify risk of concussion. The concussion algorithm may be used to generate and evaluate concussion information. Concussion information and related traumatic events may be presented to a user as a graphic visualization that can be displayed on the user device 114, 116, 118. After evaluating the concussion information, an alert or alarm may be provided to the user device 114, 116, 118 when, for example, the user device 114, 116, 118 calculates a high of probability that a subject may have experienced concussion from recent traumatic impact events, and/or is at increased risk of suffering concussion from impending or expected future traumatic impacts.

Figure 2:
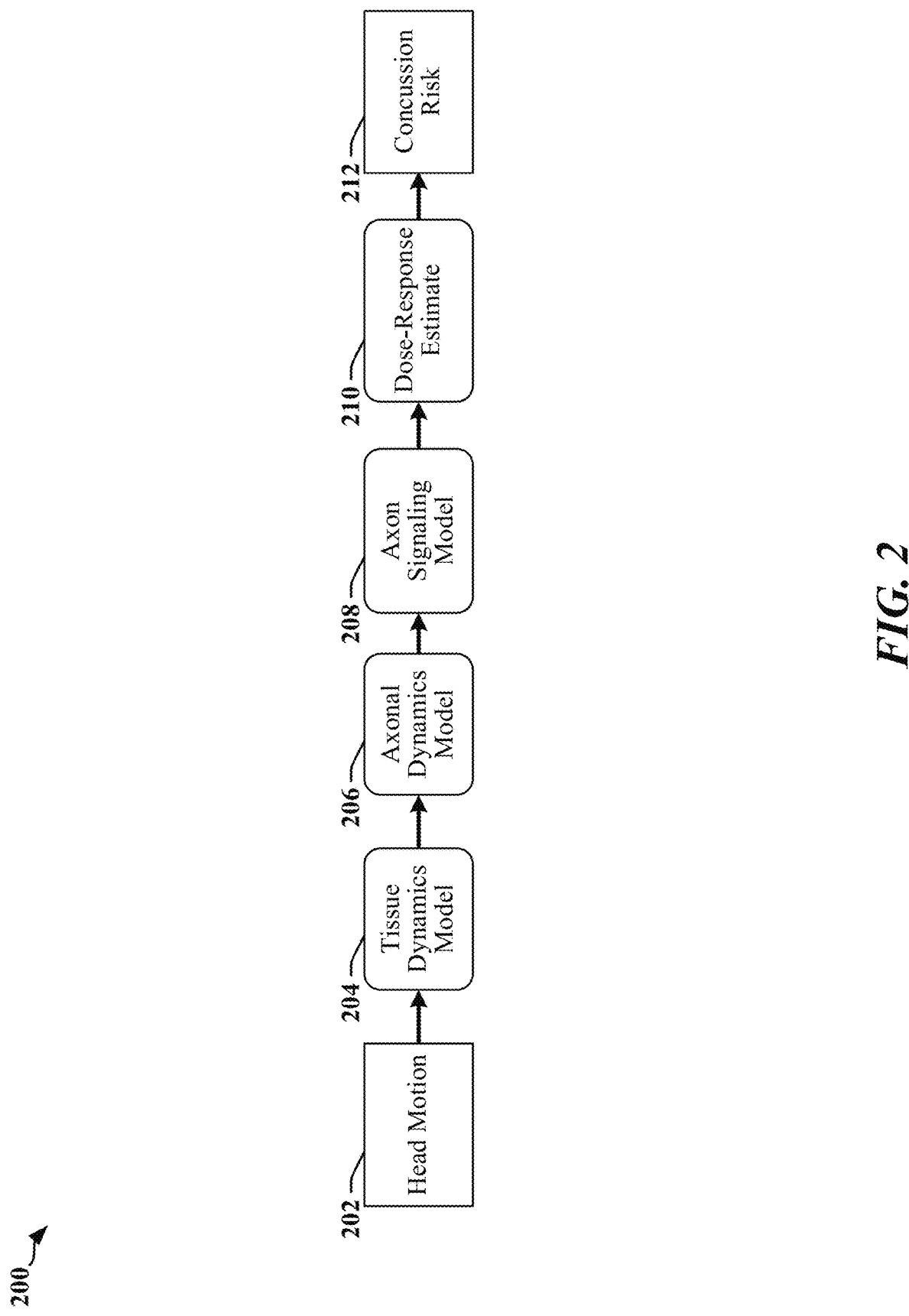
FIG. 2 illustrates a mechanistic concussion model implemented in accordance with certain aspects disclosed herein.

With reference also to FIG. 2, a concussion model 124 or mobile concussion model 122 employed in accordance with certain aspects disclosed herein may be based on, or derived from a mechanistic concussion model 200 that can characterize and quantify traumatic axonal damage to the corpus callosum of the brain and/or the brain stem. The model may quantify concussion risk 212 after a traumatic impact or blast characterized by head motion data 202 measured by a sensor platform 102. An axon may be defined herein as a nerve fiber that can conduct electrical impulses away from the body of nerve cell body and thereby enable transmission of information between neurons. The corpus callosum may be a flat bundle of axons having a length of about 10 cm that connect the two hemispheres of the brain beneath the cerebral cortex in the brain. The corpus callosum enables communication between right and left hemispheres.

Certain aspects disclosed herein relate to a validated, predictive model of mTBI that can be constructed by incorporating biomechanical, physiological, and neurological models 204, 206, 208 that can quantify or predict traumatic axonal damage. In some implementations, a relationship between dose (measure of trauma and/or severity) and symptom and/or outcome may be calculated or predicted using a dose-response estimate 210. The presence of symptoms associated with axonal damage to specific regions of the brain, such as the corpus callosum and/or the brain stem may indicate mTBI. Traumatic axonal damage occurs from deformation of the surrounding brain tissue and is accentuated by high rates of deformation. The damaged axon can partially recover from a single event but injury severity can accumulate over multiple traumatic events. Brain tissue deformation in critical regions is driven by the internal biomechanics created by violent motion of the head. In some aspects of this disclosure, a mTBI outcome may be determined from motion data obtained from sensors that monitor and quantify traumatic events.

The mobile concussion model 122 analyzes kinematics data at the center of gravity of the brain that can relate external motion data to internal strain estimates in specific regions of the brain. The mobile concussion model 122 may be employed to evaluate concussion risk by analyzing motion data captured by wearable sensors in the sensor platform 102 and to provide an individualized assessment of exposure conditions for a subject wearing components of the sensor platform 102. In one example, the mobile concussion model 122 is derived from a mechanistic concussion model 200 that employs end-to-end, science-backed concussion risk modeling adapted to quantify concussion risk from complex head kinematics. A fully-developed mechanistic concussion model 200 can be computationally expensive and may be unsuited for use in mobile user devices 114, 116, 118. The mobile concussion model 122 may represent a fast concussion risk model that can be optimized for use in a mobile communication or computing device in order to quickly and efficiently produce reliable assessments of concussion information.

Head motion data 202 received at a mobile device may be abstracted, normalized and/or transformed to represent kinematics at the center of gravity of the brain for use by the concussion model 200. In one example, placement of wearable sensors may vary between uses, and a sensor adaptation function or circuit may be employed to configure scaling factors, offsets and other adjustments to the sensor output. In another example, the sensor adaptation function or circuit may be operable to accommodate difference in outputs produced by different sensors, sensors models, types, and/or manufacturers.

Figure 3:
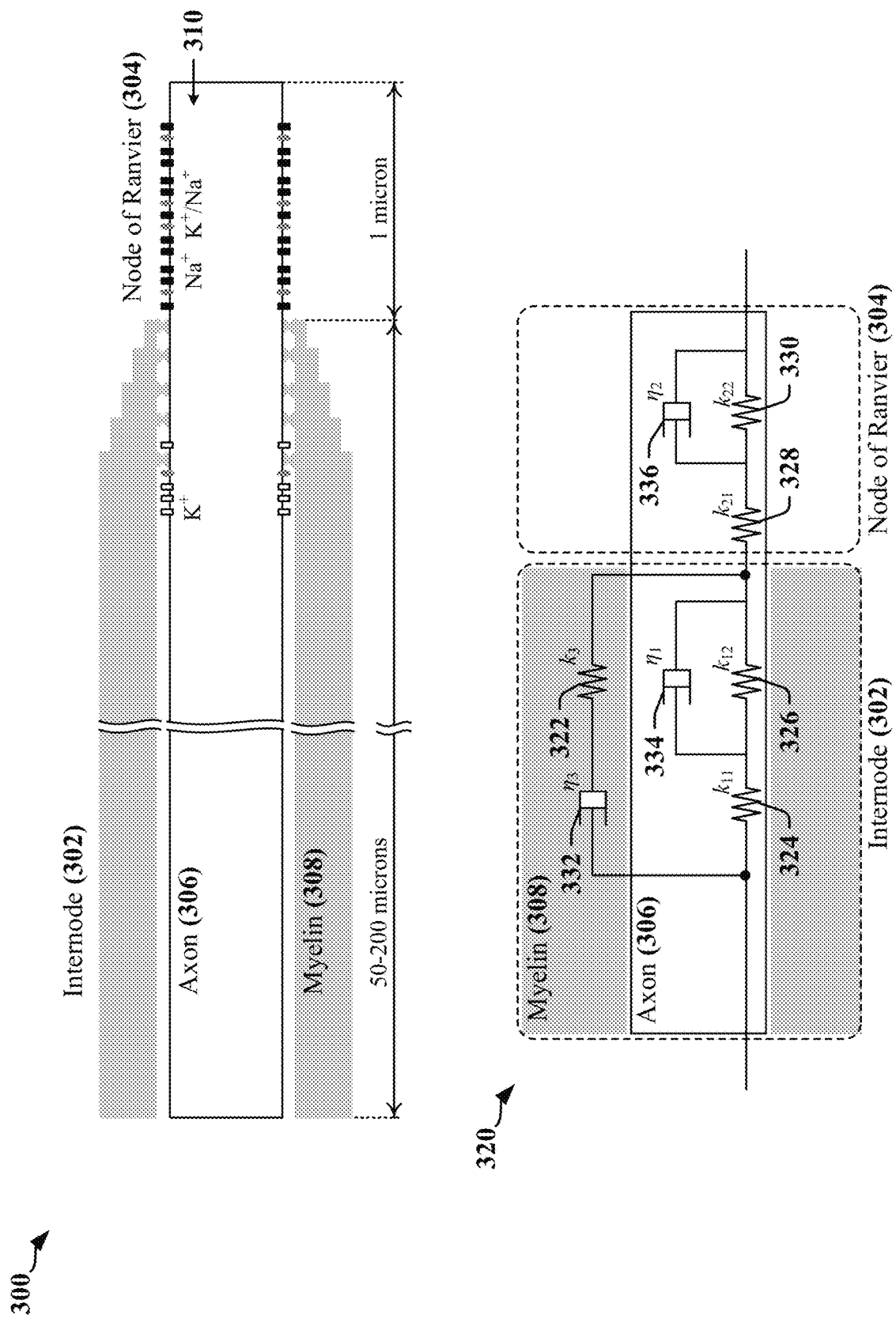
FIG. 3 illustrates an axonal micromechanics model that can characterize certain mechanical aspects of the microstructure of a myelinated axon in accordance with certain aspects disclosed herein.

FIG. 3 illustrates an axonal micromechanics model 320 that can characterize certain mechanical aspects of the microstructure of a myelinated axon 300. The myelinated axon 300 includes a myelinated internodal region 302 and an unmyelinated node of Ranvier 304. Viscoelastic micromechanical behavior of the myelinated axon 300 may be modeled under the assumption that the myelin layer 308 in the internode region 302 exhibits greater viscous behavior than the relatively elastic axon 306, with the difference being largely attributable to the myelin layer 308.

The axon model 320 includes multiple spring elements 322, 324, 326, 328, 330 and viscous damping elements 332, 334, 336 with damping constants calculated based on the nature of the modeled regions 302, 304. The axonal micromechanics model 320 may be configured to capture the relatively viscous behavior of the myelin layer 308 and the relatively elastic behavior of the underlying axon 306, and thereby to account for rate-dependent response of a composite structure. In the axonal micromechanics model 320, strain localized at the nodes of Ranvier 304 depends on axonal strain and strain rate. In some implementations, strain rate may be closely correlated with higher concussion risk. The difference in viscoelasticity between the myelin layer 308 and the underlying axon 306 can result in high strain rates in the internode 302 producing stiffening of the internode 302 and strain concentration at the node of Ranvier 304. The magnitude of strain in the node of Ranvier 304 can be more than four times the overall axonal strain for certain axonal strain rates. The relatively long sections of the viscous myelin layer 308 are interrupted by short, non-myelinated regions at the nodes of Ranvier 304, causing the nodes of Ranvier 304 to be susceptible to strain concentration at high strain rates.

Physical stretching of the node of Ranvier 304 beyond can lead to injury on the subcellular level. Nodal injury can strongly affect axonal signal propagation. The node of Ranvier 304 contains a high concentration of voltage-gated Na+ channels 310 that can be injured by physical stretching when the node of Ranvier 304 is under strain. The Na+ channels 310 are important for regeneration and propagation of action potentials along the axon 306. When subjected to stretch injury, nodal tetrodotoxin-sensitive voltage-gated Na+ channels 310 may be injured and a stretch-magnitude dependent shift in channel activation and inactivation voltages may result, which can trigger a cascade of ion redistribution events such as an influx of calcium ions. Stretch injury can result in axonal signaling dysfunction of the action potential and/or axonal degeneration.

In some implementations, the mechanistic concussion model 200 may use axonal signaling dysfunction as an internal injury metric of concussion. The mechanistic concussion model 200 may be adapted to quantitatively estimate neurological injury or risk of neurological injury from head kinematics related to axonal tensile stretching and subsequent damage to the node of Ranvier 304. In some implementations, the mechanistic concussion model 200 can identify a range of exposure types and conditions based on the model of the internal injury. The mechanistic concussion model 200 can be used to guide development of protective equipment, set safety standards, and improve monitoring technologies.

In certain examples, the mechanistic concussion model 200 includes a multi-scale set of validated component models that can relate head kinematics to axonal signaling dysfunction in the corpus callosum. The mechanistic concussion model 200 receives head motion data 202 indicative of kinematics at the center of gravity of the head. A finite-element model may process the head motion data 202 and provide an output that can be used to calculate transient axonal strains in the elements of the corpus callosum. The transient axonal strains may be translated into localized axonal strains and injury of the axonal nodes of Ranvier 304 using the micromechanical model 320 of the myelinated axon 300. Physical injury can be captured as signaling dysfunction by a biophysical signaling model that relates injury of nodal tetrodotoxin-sensitive voltage-gated Na+ channels 310 to injury-induced changes in the amplitude and latency of action potentials propagating along the injured axons 306. From this, a neurologic injury measure (NIM) can be calculated. In one example, the NIM value may represent averaged amplitude degradation of all axons over a neurologic structure, such as the corpus callosum. For instance, the NIM may be calculated by volume-weighted averaging signal dysfunction over all elements, or nodes of Ranvier 304, in the corpus callosum. A dose-response curve may be generated using the NIM, which can be used as an internal injury correlate. An axon signaling model 208 may relate localized strain associated with the axon 326 to signaling dysfunction. By accounting for axonal structure and material behavior, nodal strain can be correlated with signal dysfunction.

The mechanism-driven nature of the mechanistic concussion model 200 can avoid the inherent limitations of conventional models, and can unify concussion datasets gathered from a range of conditions, including a sports environment, a combat environment, and data gathered from animals (e.g., non-human primates), without the need for scaling. The mechanistic concussion model 200 enables estimation of risk of concussion based on disruption of neurological tissues in areas of the brain affected by injury. The extent of axonal injury may be related to the magnitude, rate, and direction of deformation may be determined from head motion data.

Figure 4:
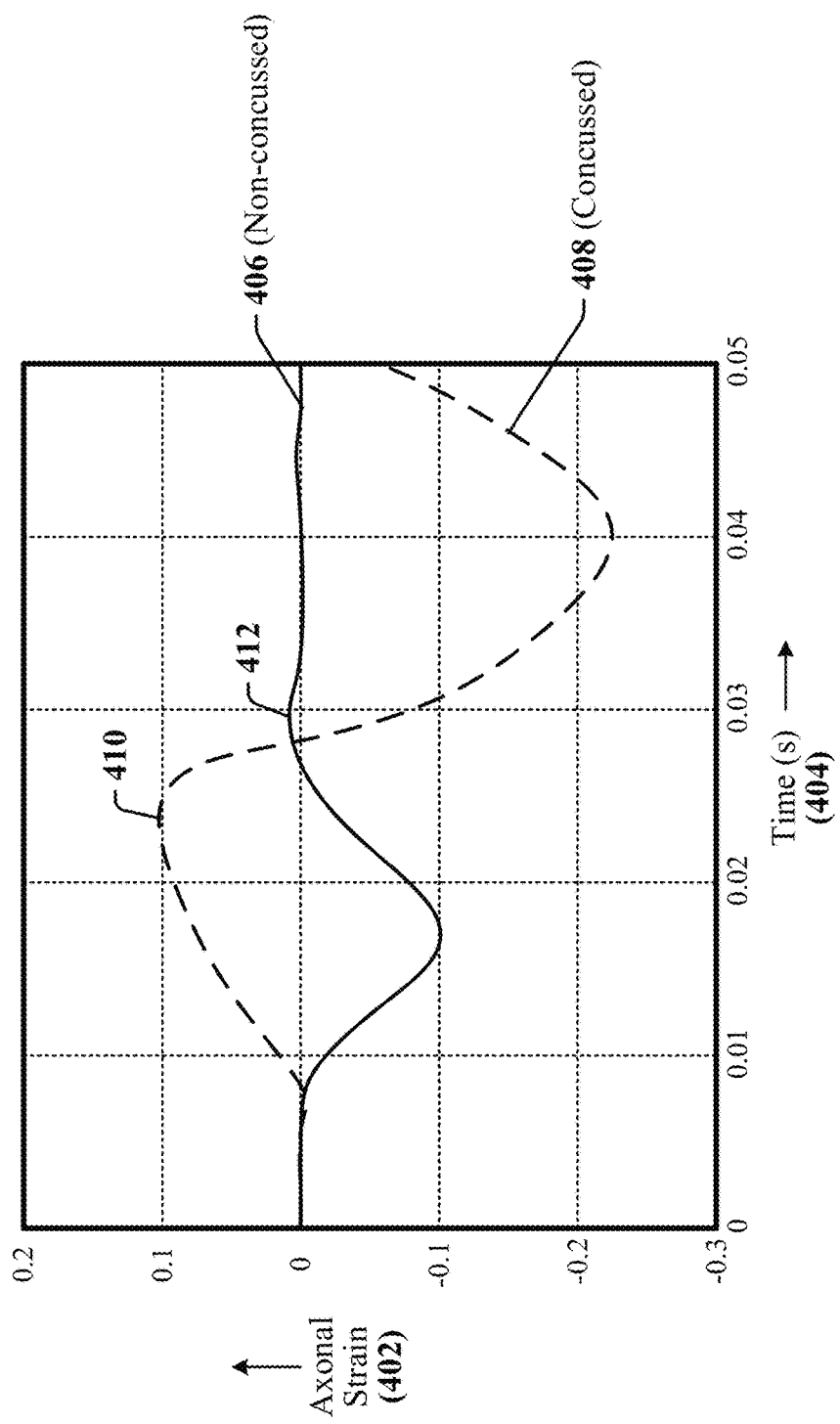
FIG. 4 is a curve illustrating axonal strain characteristics over time.
Figure 5:
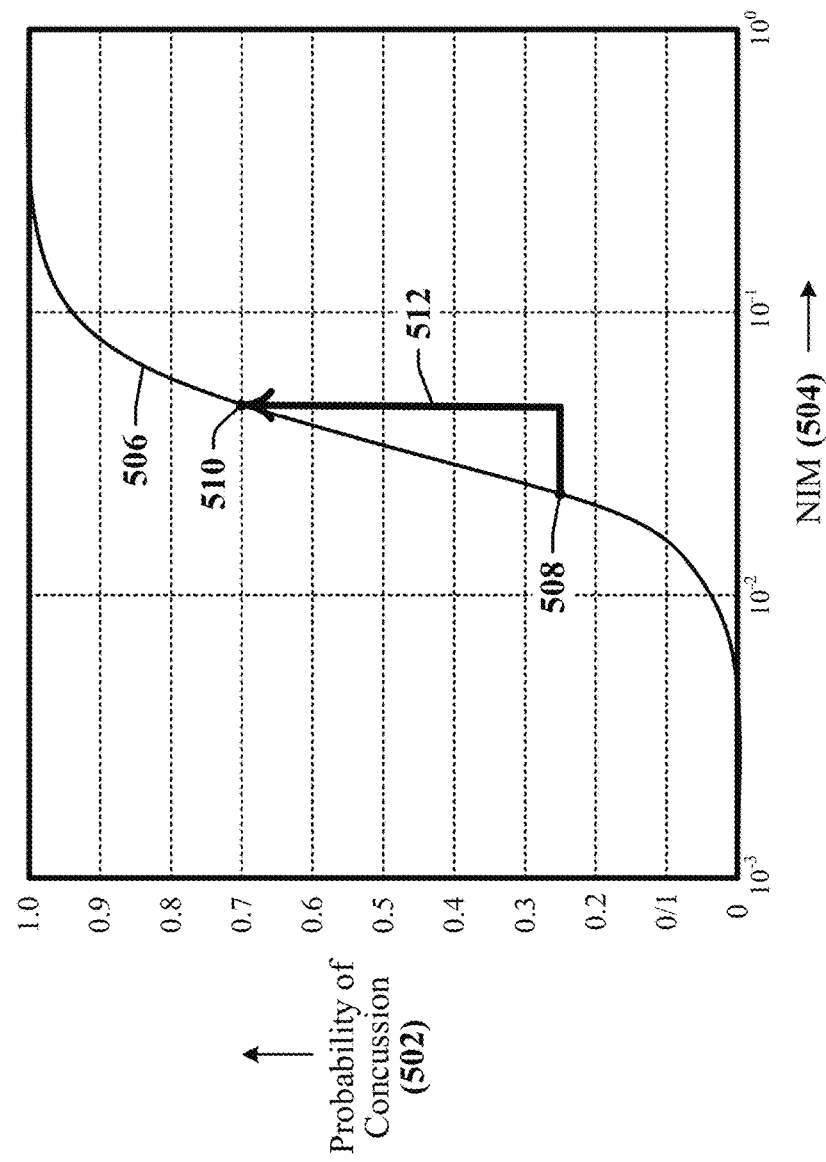
FIG. 5 illustrates a dose-response characteristic in accordance with certain aspects disclosed herein.

In certain implementations, NIM is calculated based upon axonal signaling decrement over the corpus callosum. In one example, a tissue dynamics model 204 may relate to head-neck-brain dynamics and may be based on axonal strain characteristics 400 (see FIG. 4) relating to axonal strain 402 over time 404. A concussed characteristic 408 may exhibit a higher positive peak strain value 410 than the positive peak strain value 412 in a non-concussed characteristic 406. Peak strain values 410, 412 correspond to peak values of axonal tension. Maximum values of axonal tension can highlight where injuries may concentrate in corpus callosum.

An axonal dynamics model 206 may include a micromechanics model of an axon that links directional axonal tissue strain to localized strain along the axon. A simplified axon structure can account for nodal and internodal lengths and diameters and thickness of one or more myelin layers of the axon. The axonal dynamics model 206 may be scaled for multiple axons. The axonal dynamics model 206 may be used to model localized strain along the axon.

The axon signaling model 208 may be adapted to translate physical damage to functional damage to the axons. The axonal dynamics model 206 may be used to estimate localized strain along the axons and to identify or determine when structural damage to the axon has occurred. In one example, the strain estimated at the node of Ranvier may be correlated to functional damage that manifests as axon signaling dysfunction of the action potential.

In accordance with certain aspects disclosed herein, a dose-response characteristic 500 may be based upon the end-to-end mechanistic concussion model 200 linking head kinematics to the internal NIM. A curve 506 may characterize probability of concussion 502 by NIM value 504. In one example, the NIM serves as a representation of internal dose, which can be correlated to injury outcomes. For example, an input of 6 degree-of-freedom (6 DOF) kinematics at the center of gravity of the subject's head may be determined to be indicative of a risk of concussion. The use of a calculated internal dose, rather than an external correlate, enables the algorithm to be applied under a broad range of operating conditions. The internal dose measurement disclosed herein can be applied universally, whereas external-based correlates such as peak head acceleration are dependent on the conditions in which the data has been collected and have limited applicability.

The dose-response characteristic 500 may be used to characterize the effect of multiple injuries. For example, a subject may have sustained a first injury that results in a first NIM/probability coordinate 508. A subsequent injury may have an effect 512 that results in a second NIM/probability coordinate 510 indicating increased probability of concussion.

Examples of a Concussion Model for a Mobile Platform

According to certain aspects, a local, fast concussion model may be deployed as a library in smartphones 114, smartwatches 116, tablet computers 118 and other portable devices. The library may be compatible with a programming interface provided by an operating system of the smartphone, tablet computer or other portable device may be compatible with an iOS™ or Android™ operating system and/or a programming language available for the smartphone, tablet computer or other portable device and operating system. The library can implement the mobile concussion model 122, and typically enables performance of calculations related to an impact within a few seconds. Near-instant feedback can be provided to the user regarding the outcome of the event. The feedback may include a concussive risk assessment for each event. The concussive risk assessment may be stored locally, communicated to network storage, and a visualization may be provided for display on a mobile device.

According to certain aspects, the library may enable a user processing platform 104 to map specific configurations of sensors and motion data generated by the sensors to a local, fast concussion model. The local, fast concussion model permits external motion data to be expressed as internal axonal strains and axonal signaling dysfunction. The mapping of external motion data in this manner enables NIM values to be reliably and consistently calculated independently of sensor platform configuration. For example, aspects of the disclosure enable a first NIM/probability value (represented as the coordinate 508) and the second NIM/probability value (represented as the coordinate 510) in the dose-response characteristic 500 to be calculated using different configurations of sensors.

Sensors incorporated in the sensor platform 102 can be characterized based on type of sensor, placement, sensitivity, sampling rates, etc. The library may provide transforms, parameters and descriptors that can be used to integrate the configuration of sensors into the local, fast concussion model. In one example, the local, fast concussion model may be derived from a more complex finite element model representing the dynamics of the head and brain. The finite element model translates head motion into dynamic strains along the axons in the brain. To expedite this calculation for portable and/or mobile devices, a simplified brain dynamics model may be derived, which may be one piece of the full mechanistic concussion model, from which NIM is calculated. The finite element model may link kinematics to dynamic strains in the direction of the axon in the brain, where the motion of defined points, objects, and groups of objects can be determined from motion data provided by the sensor platform 102. The library may enable rapid calculation of NIM values based on baseline information obtained using the mechanistic concussion model 200. In some instances, calculations and/or estimates generated by the mobile concussion model 122 used by the user processing platform 104 may be integrated into the mechanistic concussion model 200 as feedback.

Examples of a Sensor Platform

Figure 6:
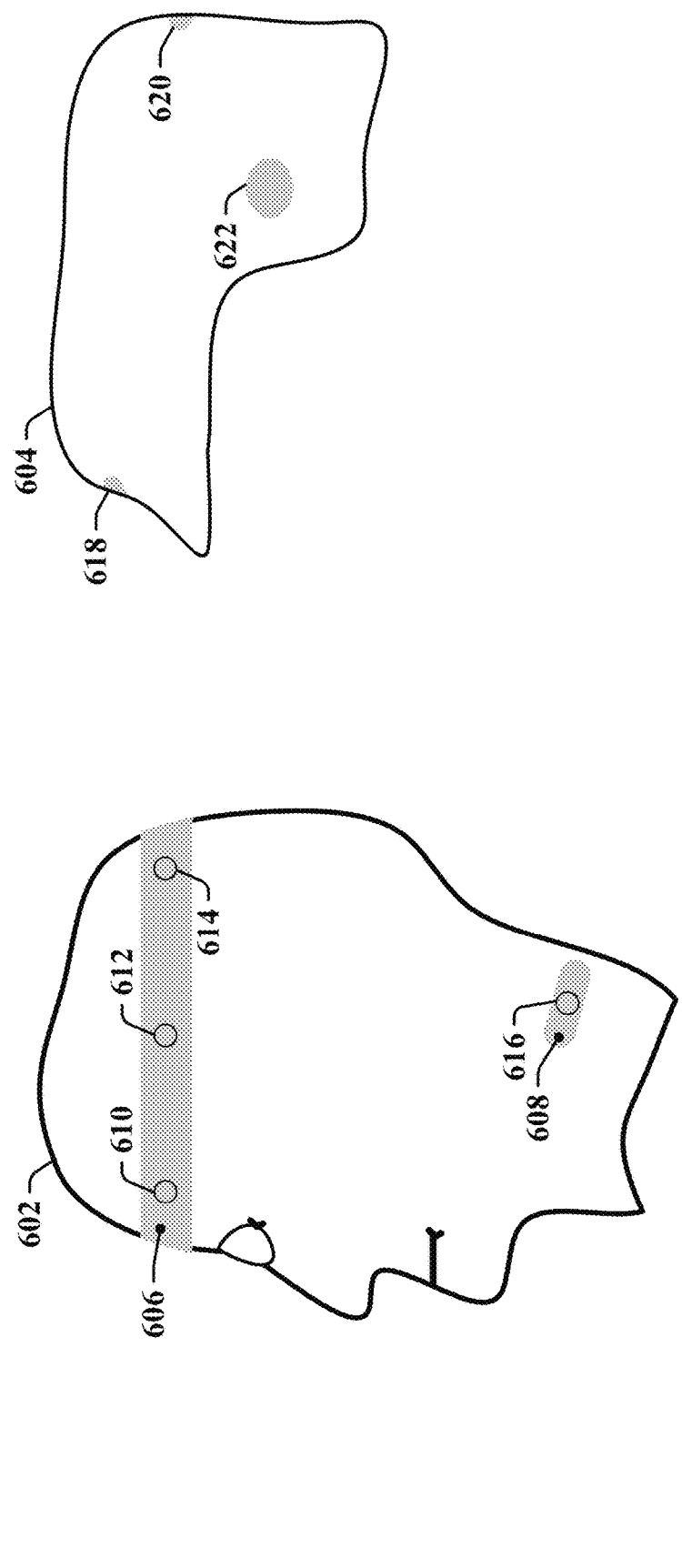
FIG. 6 illustrates a sensor platform that may be implemented in accordance with certain aspects disclosed herein.

FIG. 6 illustrates a sensor platform 600 that includes sensor devices 610, 612, 614, 616, 618, 620, 622 deployed using a variety of carriers 604, 606, 608. Each of the illustrated sensor devices 610, 612, 614, 616, 618, 620, 622 may include a single sensor, a cluster or array of sensors, and/or a controller that operates one or more sensors and communicates with a monitoring device. According to certain aspects disclosed herein, any sensor platform 600 that collects meaningful head motion data and implements a supported data communication protocol can be used.

In one example, a sporting helmet, a combat helmet, a hat, or another type of head cover 604 may carry sensor devices 618, 620, 622 in a spatial configuration that can capture motion data in multiple dimensions. In another example, a headband 606 may carry sensor devices 610, 612, 614 in a desired arrangement around a subject's head 602. Other sensor devices 616 may be positioned on individual carriers or carriers that locate a small group or cluster at a desired location on the head 602. For example, sensor devices may be provided in a mouth guard, within an ear (mounted on an earpiece for example) and/or mounted in eyewear.

The sensor platform 600 may be calibrated using the library installed by the user processing platform 104. The user processing platform 104 may determine relative locations and proximities of individual sensors and groups of sensors based on ordinary non-traumatic motions and/or based on descriptions of subcomponents of the sensor platform. For example, the relative locations of sensor devices 610, 612, 614, 616, 618, 620, 622 may be known to a substantial degree of accuracy, and motion information from these sensor devices 618, 620, 622 may be used to calibrate the sensor platform 600.

The sensor platform 600 may include a variety of sensor systems that can collect head motion data from which head motion can be accurately determined. A sensor platform 600 must typically communicate using a data communication protocol used by the user processing platform 104. In one example, the Bluetooth data communication protocol may be employed by the sensor devices 610, 612, 614, 616, 618, 620, 622 and/or sensor platform 600 to share data through some combination of wireless, wired, or inter-process communications. A mobile concussion model 122 may specify a level of fidelity of sensor data necessary to provide meaningful data.

Data Communications

Sensor data may be communicated using a data collection API. In one example, input data includes data values representing time, x, y, z linear acceleration, and/or x, y, z rotational velocity at the center of gravity of the subject's head. The data collection API may define units of measure for each type of input data. Units of measure may be defined for time values (e.g., milliseconds), acceleration expressed in units of acceleration of gravity (g), velocity may be measured in meters per second, and so on. In some examples, data input is sampled and/or provided at a defined minimum sampling rate. In one example, the sampling rate is 20 kHz.

Data may be communicated using a standards-defined or a proprietary protocol. In one example, a mobile Bluetooth interface may be provided in a sensor platform 600 to transfer data to user processing platform 104. Data may be encrypted using a standards-defined or a proprietary protocol that provides encryption keys or tokens. Data can be collected after each event of interest, or based on a trigger that occurs after a certain length of time or number of events of interest. In some instances, data can be transmitted using an available wired interconnect. A standards-defined or a proprietary protocol may be used for wired data transmission, and data may be encrypted using a standards-defined or a proprietary protocol that provides encryption keys or tokens. In one example, stored data can be collected when the sensor platform 600 is connected to a user processing platform 104. All stored events are typically transferred when the sensor platform 600 is plugged into the user processing platform 104.

Data Storage and Visualization

Data generated by a sensor platform 600 and/or by the mobile concussion model 122 executed by the user processing platform 104 may be stored locally or on a network server. Local storage 120 and cloud-based storage 110 may provide persistent data storage that supports further analysis and recall. Cloud-based storage 110 may be provided for users with registered accounts. Data may be organized and securely stored in accordance by user account with access provided to authenticated users, parents, guardians and other authorized delegates such as coaches, training staff, etc.

Local storage 120 may be used for storing data collected from the sensor platform 600.

Data may be stored in a corresponding device application storage area of a smartphone 114, smartwatch 116, tablet computer 118 or another portable device. In one example, data for each event can be stored in approximately 10 kB of memory, depending on sampling frequency of sensor platform 102, and over 10,000 events can be easily stored on an average mobile device. Data can be stored locally for a user-defined period of time, and/or until backed up in cloud-based storage 110. In some implementations, the user can specify how much data is to be stored locally and/or retrieved from cloud-based storage 110. In some implementations, metadata can be attached to traces to identify key metrics concerning each event. The user may add information about event if known. Metadata and concussion risk model output can be stored locally or on cloud-based storage 110.

The system may utilize cloud storage to maintain persistent event and concussion risk data. Data may be accessible from a mobile application for the purpose of visualization previous events. Data may be stored and used to develop more advanced algorithms based on aggregate comparison of data collected over multiple subjects. In one example, data associated with similar subjects can be compared and provided in a comparative visualization to user.

Cloud-based storage 110 may be used to provide quick access to data visualization. Sensor data may be visualized on a mobile device using interactive plots, and/or in a manner that displays data in a meaningful manner. Concussive risk model outcomes can be presented to user in meaningful visualizations. Relevant personal data may be editable through a mobile application operated by an authorized user. In some examples, partner sensor platforms will be editable and visible through applications deployed on a mobile device.

Data visualization tools may be developed using platform-specific development environments. In one example, Apple™ iOS Swift Programming language may be used to develop visualization tools. Visualization tools may provide authentication and other security features and may store credentials and/or access credentials through native security applications.

In one example, visualization tools provide a menu of options, including options providing submenus for Events, Sensors, Settings, etc. Main content window will show a current selected menu option. The Events submenu or main screen may show a history of events organized by most recent events and/or by severity. In some instances, high category events (e.g., greater that 50% probability of concussion) may be flagged for user attention. In many examples, data for visualization can be seamlessly downloaded from cloud-based storage 110.

In another example, visualization tools provide a display of currently-connected sensors. Currently-connected sensors may be clearly visible on the display while other unconnected sensors may be selected for configuration. Configuration may include configuring connections to sensors and adding new sensors to application.

In another example, visualization tools provide a settings mode in which metadata about the individual user and/or application settings can be defined.

Eye-catching visualization of data can clearly distinguish high-risk concussive events. In one example, high-risk concussive events are made visible on a main page so that the user can click on an event to get more visual details regarding the event. Detailed plots may be provided to show acceleration/velocity curves of the head. Other detailed plots may identify concussive injury probability on a dose response curve 506. Concussive injury probabilities for different events experienced by the subject may be displayed such that the subject can compare the effects of the specific events. Interactive graphic displays may be used to show simulated head motion based on input data. The graphic displays may indicate where initial impact most likely occurred and the motion resulting from the impact. Highlights may be added where multiple hits are likely. Available metadata is may be used to link event data to known time events. In one example, in-game sports traumatic event data collection may be matched to game time video. In another example, information regarding a subject's mass, position and/or other relevant known characteristics can be provided to provide insight to the traumatic event. Content may be developed through data mining of collected data and available metadata.

Example of a Fast-Running Concussion Risk Model

The mechanistic concussion model 200 illustrated in FIG. 2 can be used to associate human head motion to a NIM, where the NIM can be calculated by volume-weighted averaging of signal dysfunction over the axons of the corpus callosum. The NIM serves as the internal dose correlate that can be considered robust with respect to a range of exposure and boundary conditions. The mechanistic concussion model 200 incorporates biomechanical, physiological, and neurological processes associated with concussion in component models. Use of the mechanistic concussion model 200 can be a complex and computationally-intensive process.

Figure 7:
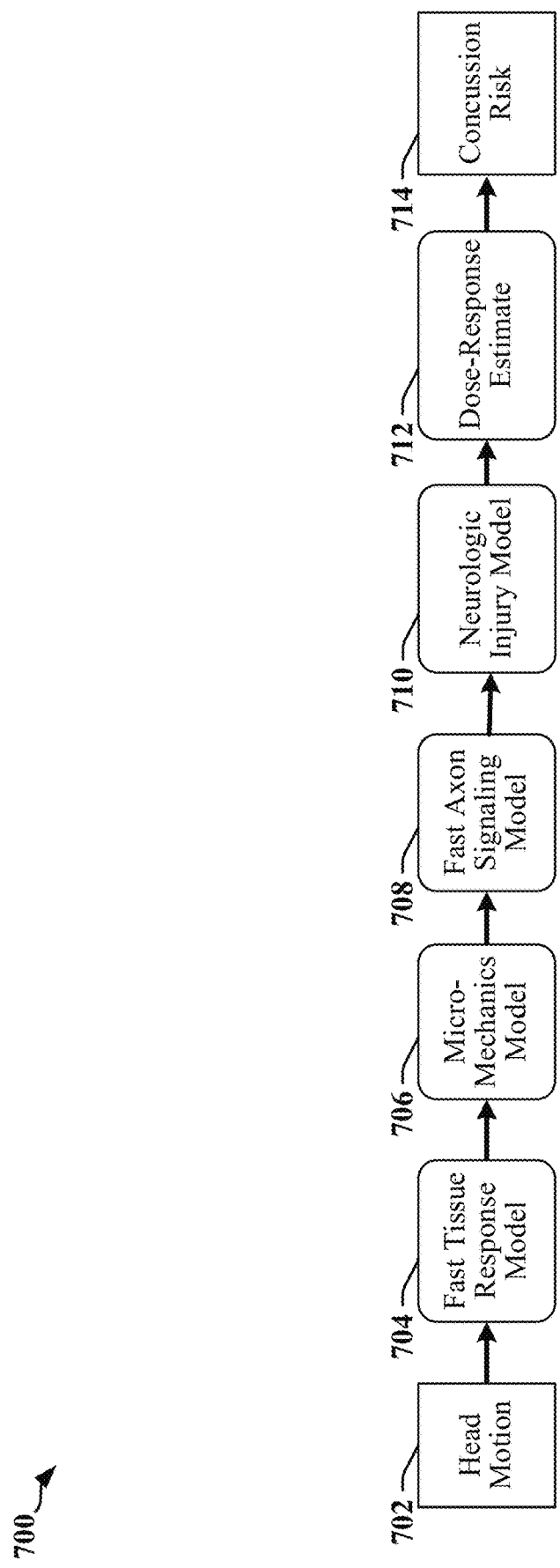
FIG. 7 illustrates an example of a fast-running concussion risk model derived from an end-to-end mechanistic concussion model in accordance with certain aspects disclosed herein.
Figure 8:
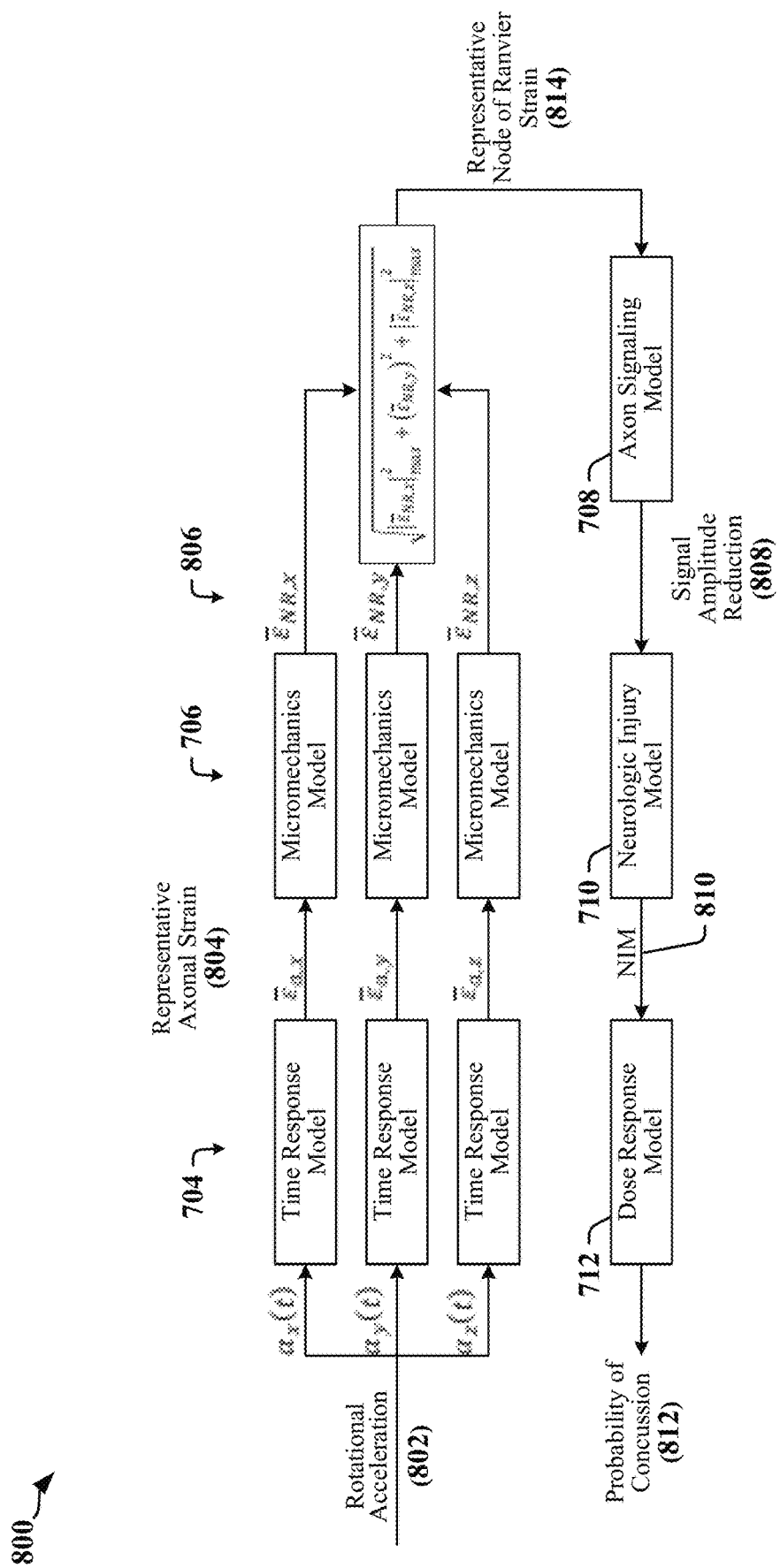
FIG. 8 illustrates a mathematical model corresponding to the fast-running concussion risk model of FIG. 7.

According to certain aspects disclosed herein, a fast-running process can be deployed on mobile communication devices that enables rapid, real time analysis of complex head impacts and accelerations to produce risk assessments of concussion. FIG. 7 illustrates an example of a fast-running concussion risk model 700 that is derived from the mechanistic concussion model 200. The fast-running concussion risk model 700 may be implemented by reducing the dynamic axonal response of the human head finite element model to head motion and the axonal signaling component into efficient algorithms, as illustrated in the mathematical model 800 of FIG. 8. In one example, translation may be accomplished using a lumped parameter approach. The fast-running concussion risk model 700 assumes that linear acceleration insignificantly affects axonal strains, and provides on angular components of the rotational acceleration 802 as inputs to a fast-running tissue-response model 704. In this example, the representative axonal strain 804 is provided by the fast-running tissue-response model 704 to a micromechanics model 706 that generates estimates of the strain at the node of Ranvier ($\varepsilon$NR) 806 for each angular component. A processor may execute an algorithm (see the micromechanics model 706) that produces a representation of node of Ranvier strain 814, which is provided to an axon signaling model 708. The axon signaling model 708 may estimate a signal amplitude reduction 808 characterizing the effects of node of Ranvier strain. This estimated signal amplitude reduction 808 can be used by a neurologic injury model 710 to produce the NIM 810 which is fed to a dose response model 712. The dose response model 712 can be configured to produce a probability of concussion 812.

The fast-running concussion risk model 700 may be employed in the sporting and military arenas. The fast-running concussion risk model 700 can be integrated with wearable head/helmet impact sensors that can characterize accelerative loads sustained by the head and that can be used to identify injured individuals. The fast-running concussion risk model 700 account for directionality effects of extraordinary acceleration events which result from impacts and/or from an application of an accelerative load to the subject's body.

In various implementations, the fast-running concussion risk model 700 or portions of the fast-running concussion risk model 700 can be embedded in wearable sensors, which may be operable as dosimeters that can accurately identify concussed individuals in near-real time for a range of exposure environments. The fast-running concussion risk model 700 or a derivative thereof may be provided as the mobile concussion model 122 executed by the user processing platform 104 in FIG. 1.

Examples of Processing Devices and Methods

Figure 9:
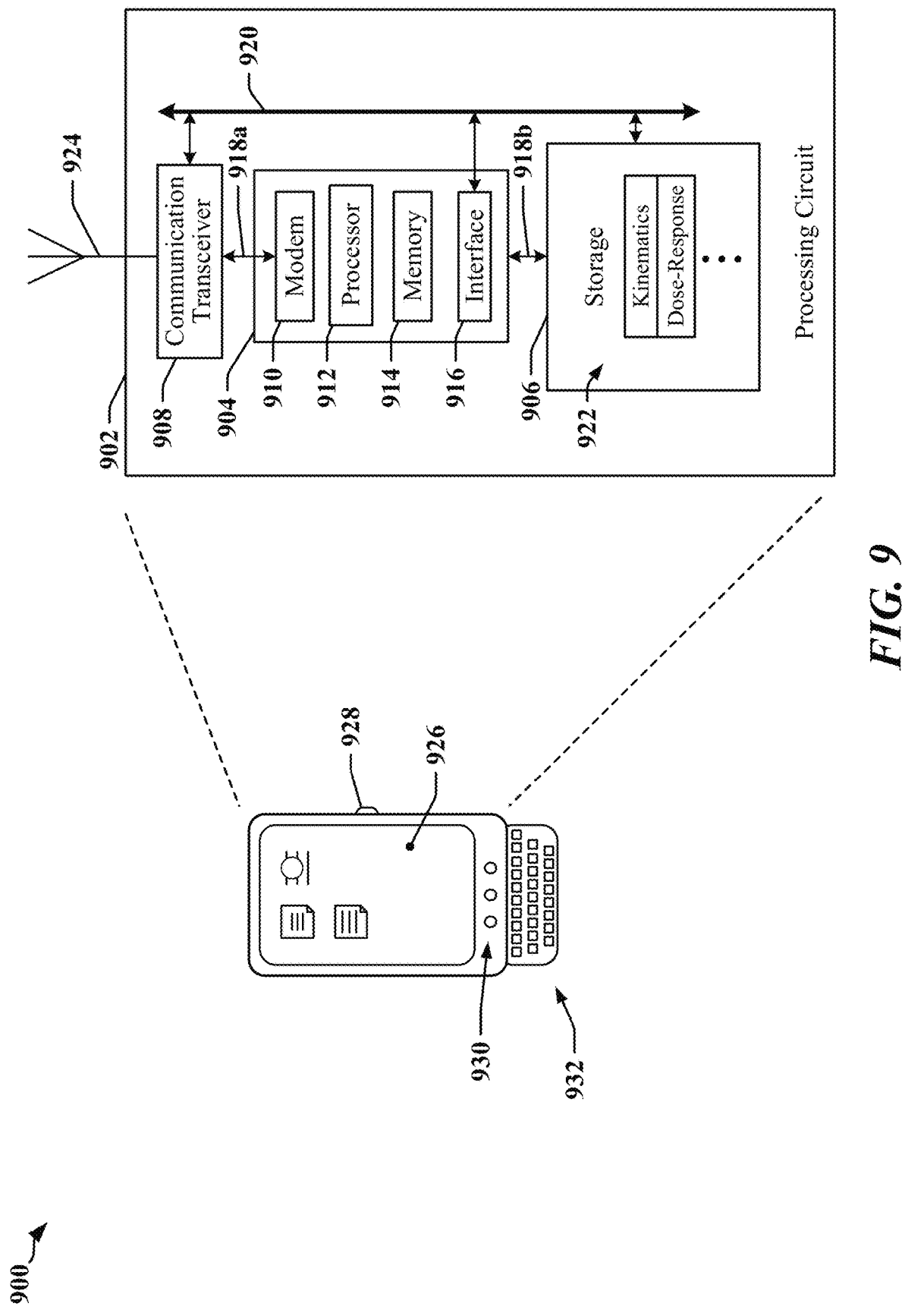
FIG. 9 illustrates an example of a portable computing device that may be adapted in accordance with certain aspects disclosed herein.

FIG. 9 illustrates an example of an apparatus 900 that may be operated as the user processing platform 104. The apparatus 900 may include a processing circuit 902 having multiple circuits or devices 904, 906 and/or 908, which may be implemented in one or more application-specific integrated circuits (ASICs) or in a system-on-chip (SoC). In one example, the apparatus 900 may be a wireless communication device and the processing circuit 902 may include a processing device 904, one or more storage devices 906, and a transceiver 908 that enables the apparatus to communicate through an antenna 924 with a wireless network, a cellular radio access network, the Internet and/or another network.

The processing device 904 may have one or more processors 912, one or more modems 910, on-board memory 914, a bus interface circuit 916 and/or other logic circuits or functions. The processing circuit 902 may be controlled by an operating system that may provide an application programming interface (API) layer that enables the one or more processors 912 to execute software modules residing in the on-board memory 914 or other processor-readable storage 906 provided on the processing circuit 902. In one example, the processor-readable storage 906 may include elements 922 associated with a concussion algorithm. The software modules may include instructions and data stored in the on-board memory 914 or processor-readable storage 906. The on-board memory 914, the processor-readable storage 906 may include read-only memory (ROM) or random-access memory (RAM), electrically erasable programmable ROM (EEPROM), flash cards, or any memory device that can be used in processing systems and computing platforms. The processing circuit 902 may include, implement, or have access to a local database or other parameter storage that can maintain operational parameters and other information used to configure and operate the apparatus 900 and/or the processing circuit 902. The local database may be implemented using registers, a database module, flash memory, magnetic media, EEPROM, soft or hard disk, or the like. The processing circuit 902 may also be operably coupled to external devices such as the antenna 924, a display 926, operator controls, such as switches or buttons 928, 930 and/or an integrated or external keypad 932, among other components. A user interface module may be configured to operate with the display 926, keypad 932, etc. through a dedicated communication link or through one or more serial data interconnects.

The processing circuit 902 may provide one or more buses 918a, 918b, 920 that enable certain devices 904, 906, and/or 908 to communicate. In one example, the processing device 904 may include a bus interface circuit 916 that includes a combination of circuits, counters, timers, control logic and other configurable circuits or modules. In one example, the bus interface circuit 916 may be configured to operate in accordance with standards-defined communication specifications or protocols. The processing circuit 902 may include or control a power management function that configures and manages the operation of the apparatus 900.

Figure 10:
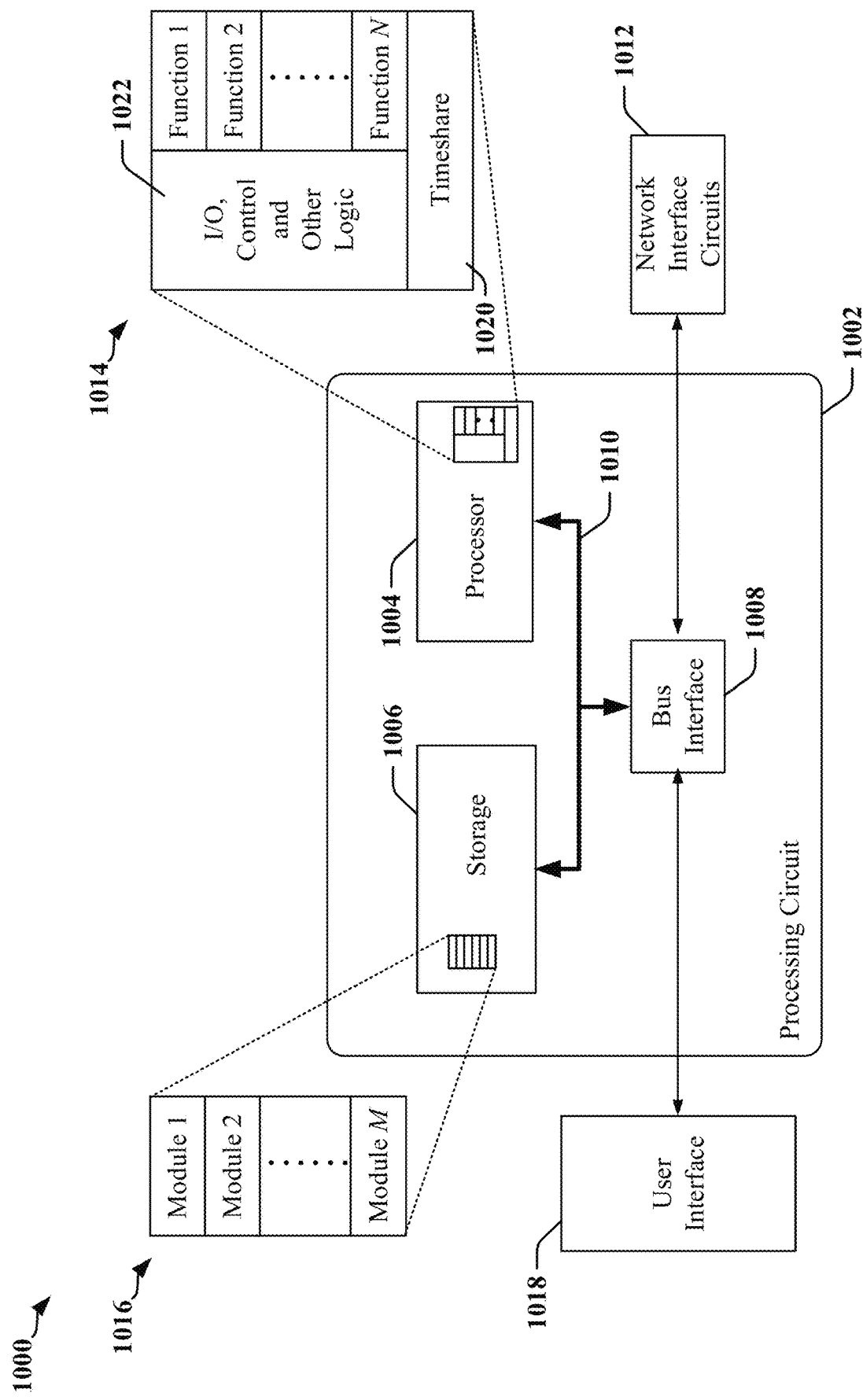
FIG. 10 illustrates an apparatus employing a processing circuit that may be adapted according to certain aspects disclosed herein.

FIG. 10 is a conceptual diagram illustrating a simplified example of a hardware implementation for an apparatus 1000 employing a processing circuit 1002 that may be configured to perform one or more functions disclosed herein. In accordance with various aspects of the disclosure, an element, or any portion of an element, or any combination of elements as disclosed herein may be implemented using the processing circuit 1002. The processing circuit 1002 may include one or more processors 1004 that are controlled by some combination of hardware and software modules. Examples of processors 1004 include microprocessors, microcontrollers, digital signal processors (DSPs), ASICs, field programmable gate arrays (FPGAs), programmable logic devices (PLDs), state machines, sequencers, gated logic, discrete hardware circuits, and other suitable hardware configured to perform the various functionality described throughout this disclosure. The one or more processors 1004 may include specialized processors that perform specific functions, and that may be configured, augmented or controlled by one of the software modules 1016. The one or more processors 1004 may be configured through a combination of software modules 1016 loaded during initialization, and further configured by loading or unloading one or more software modules 1016 during operation.

In the illustrated example, the processing circuit 1002 may be implemented with a bus architecture, represented generally by the bus 1010. The bus 1010 may include any number of interconnecting buses and bridges depending on the specific application of the processing circuit 1002 and the overall design constraints. The bus 1010 links together various circuits including the one or more processors 1004, and storage 1006. Storage 1006 may include memory devices and mass storage devices, and may be referred to herein as computer-readable media and/or processor-readable media. The bus 1010 may also link various other circuits such as timing sources, timers, peripherals, voltage regulators, and power management circuits. A bus interface 1008 may provide an interface between the bus 1010 and one or more transceivers 1012. A transceiver 1012 may be provided for each networking technology supported by the processing circuit. In some instances, multiple networking technologies may share some or all of the circuitry or processing modules found in a transceiver 1012. Each transceiver 1012 provides a means for communicating with various other apparatus over a transmission medium. Depending upon the nature of the apparatus 1000, a user interface 1018 (e.g., keypad, display, speaker, microphone, joystick) may also be provided, and may be communicatively coupled to the bus 1010 directly or through the bus interface 1008.

A processor 1004 may be responsible for managing the bus 1010 and for general processing that may include the execution of software stored in a computer-readable medium that may include the storage 1006. In this respect, the processing circuit 1002, including the processor 1004, may be used to implement any of the methods, functions and techniques disclosed herein. The storage 1006 may be used for storing data that is manipulated by the processor 1004 when executing software, and the software may be configured to implement any one of the methods disclosed herein.

One or more processors 1004 in the processing circuit 1002 may execute software. Software shall be construed broadly to mean instructions, instruction sets, code, code segments, program code, programs, subprograms, software modules, applications, software applications, software packages, routines, subroutines, objects, executables, threads of execution, procedures, functions, algorithms, etc., whether referred to as software, firmware, middleware, microcode, hardware description language, or otherwise. The software may reside in computer-readable form in the storage 1006 or in an external computer readable medium. The external computer-readable medium and/or storage 1006 may include a non-transitory computer-readable medium. A non-transitory computer-readable medium includes, by way of example, a magnetic storage device (e.g., hard disk, floppy disk, magnetic strip), an optical disk (e.g., a compact disc (CD) or a digital versatile disc (DVD)), a smart card, a flash memory device (e.g., a "flash drive," a card, a stick, or a key drive), a random access memory (RAM), a read only memory (ROM), a programmable ROM (PROM), an erasable PROM (EPROM), an electrically erasable PROM (EEPROM), a register, a removable disk, and any other suitable medium for storing software and/or instructions that may be accessed and read by a computer. The computer-readable medium and/or storage 1006 may also include, by way of example, a carrier wave, a transmission line, and any other suitable medium for transmitting software and/or instructions that may be accessed and read by a computer. Computer-readable medium and/or the storage 1006 may reside in the processing circuit 1002, in the processor 1004, external to the processing circuit 1002, or be distributed across multiple entities including the processing circuit 1002. The computer-readable medium and/or storage 1006 may be embodied in a computer program product. By way of example, a computer program product may include a computer-readable medium in packaging materials. Those skilled in the art will recognize how best to implement the described functionality presented throughout this disclosure depending on the particular application and the overall design constraints imposed on the overall system.

The storage 1006 may maintain software maintained and/or organized in loadable code segments, modules, applications, programs, etc., which may be referred to herein as software modules 1016. Each of the software modules 1016 may include instructions and data that, when installed or loaded on the processing circuit 1002 and executed by the one or more processors 1004, contribute to a run-time image 1014 that controls the operation of the one or more processors 1004. When executed, certain instructions may cause the processing circuit 1002 to perform functions in accordance with certain methods, algorithms and processes described herein.

Some of the software modules 1016 may be loaded during initialization of the processing circuit 1002, and these software modules 1016 may configure the processing circuit 1002 to enable performance of the various functions disclosed herein. For example, some software modules 1016 may configure internal devices and/or logic circuits 1022 of the processor 1004, and may manage access to external devices such as the transceiver 1012, the bus interface 1008, the user interface 1018, timers, mathematical coprocessors, and so on. The software modules 1016 may include a control program and/or an operating system that interacts with interrupt handlers and device drivers, and that controls access to various resources provided by the processing circuit 1002. The resources may include memory, processing time, access to the transceiver 1012, the user interface 1018, and so on.

One or more processors 1004 of the processing circuit 1002 may be multifunctional, whereby some of the software modules 1016 are loaded and configured to perform different functions or different instances of the same function. The one or more processors 1004 may additionally be adapted to manage background tasks initiated in response to inputs from the user interface 1018, the transceiver 1012, and device drivers, for example. To support the performance of multiple functions, the one or more processors 1004 may be configured to provide a multitasking environment, whereby each of a plurality of functions is implemented as a set of tasks serviced by the one or more processors 1004 as needed or desired. In one example, the multitasking environment may be implemented using a timesharing program 1020 that passes control of a processor 1004 between different tasks, whereby each task returns control of the one or more processors 1004 to the timesharing program 1020 upon completion of any outstanding operations and/or in response to an input such as an interrupt. When a task has control of the one or more processors 1004, the processing circuit is effectively specialized for the purposes addressed by the function associated with the controlling task. The timesharing program 1020 may include an operating system, a main loop that transfers control on a round-robin basis, a function that allocates control of the one or more processors 1004 in accordance with a prioritization of the functions, and/or an interrupt driven main loop that responds to external events by providing control of the one or more processors 1004 to a handling function.

Figure 11:
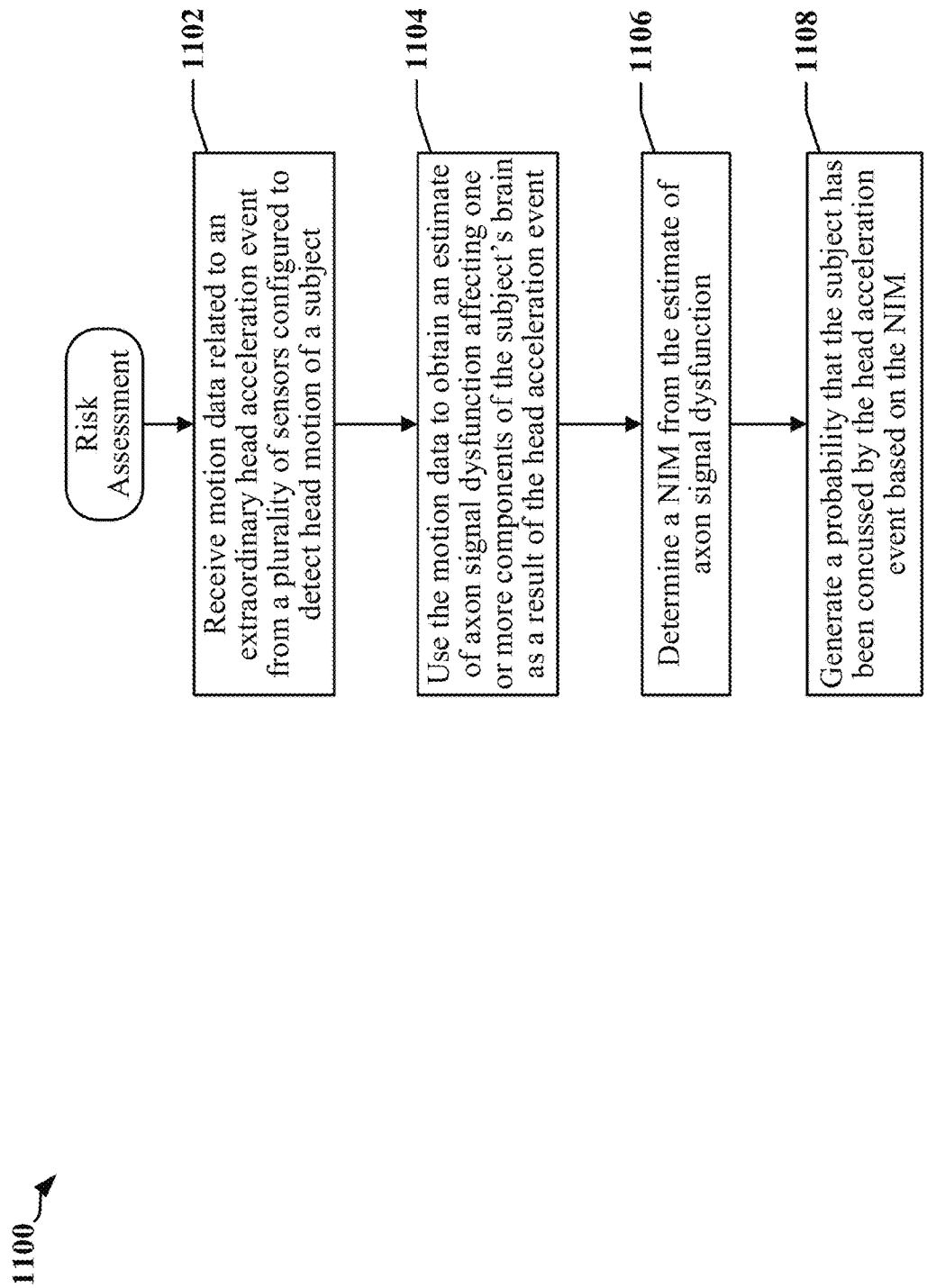
FIG. 11 is a flow chart of a method that may be implemented at a portable communication device in accordance with certain aspects disclosed herein.

FIG. 11 is a flow chart 1100 of a method that may be implemented at a portable communication device.

At block 1102, the device may receive motion data related to an extraordinary head acceleration event from a plurality of sensors configured to detect head motion of a subject.

At block 1104, the device may use the motion data to obtain an estimate of axon signal dysfunction affecting one or more components of the subject's brain as a result of the head acceleration event.

At block 1106, the device may determine a NIM from the estimate of axon signal dysfunction. The NIM may be determined using a volume-weighted average of axon signal dysfunction over a plurality of axons in the one or more components of the subject's brain. In one example, the plurality of axons includes axons located in the corpus callosum of the subject's brain.

At block 1108, the device may generate a probability that the subject has been concussed by the head acceleration event based on the NIM.

In some instances, the head acceleration event results from an impact to the subject's head or exposure of the subject's head to a blast. In some instances, the head acceleration event results from an application of an accelerative load to the subject's body.

In certain examples, the device may transform the motion data to obtain head kinematics abstracted from placement of the plurality of sensors with respect to the subject's head. At least one sensor may be mechanically decoupled from the subject's head. A sensor decoupled from the subject's head may be unattached to the subject's head or an object worn by the subject. For example, the mechanically decoupled sensor may be a camera. One or more sensor may provide a stream of image data that captures movement of the subject's head.

In some examples, the estimate of axon signal dysfunction may be obtained by determining strain at nodes of Ranvier in the one or more components of the subject's brain, and estimating axon signal dysfunction by translating the strain at the nodes of Ranvier to functional decrement of axon signaling. The strain at the nodes of Ranvier may be determined, inter alia, at nodes of Ranvier in the subject's corpus callosum.

In some examples, a probability that the subject has been concussed may be determined through the use of dose-response information obtained from a mechanistic concussion model. The dose-response information may characterize a cumulative effect of multiple extraordinary head acceleration events affecting the subject's head. The device may correlate NIM to an injury outcome using dose-response information obtained from the mechanistic concussion model. In some instances, the device may correlate the NIM to an injury outcome using a fast concussion model that employs a plurality of transforms received from a network server that maintains a mechanistic concussion model.

The motion data related to the traumatic event may be transmitted to the network server that maintains the mechanistic concussion model. Information obtained from a plurality of extraordinary head acceleration events affecting one or more subjects is used to update the fast concussion model. The device may receive one or more updated transforms from the network server that maintains the mechanistic concussion model after the fast concussion model is updated. The device may receive visualization data from the network server that maintains the mechanistic concussion model, and the device may provide a visualization of an extraordinary head acceleration event on the portable communication device.

In some examples, the device may configure the plurality of sensors based on format and timing requirements defined for an interface that transforms the motion data. The device may generate visualization data using the motion data related to the extraordinary head acceleration event and based on configuration of the plurality of sensors. The visualization of the extraordinary head acceleration event may be provided and/or displayed through the portable communication device.

In certain examples, the device may communicate with the plurality of sensors periodically using a wireless communication protocol. The motion data related to the traumatic event may be received during one or more periodic communication events. The motion data related to the extraordinary head acceleration event may be received while communicating with the plurality of sensors responsive to an indication that the extraordinary head acceleration event has occurred.

In some instances, a user of the portable communication device may be alerted when the probability that the subject has been concussed by the extraordinary head acceleration event exceeds a configured threshold.

Figure 12:
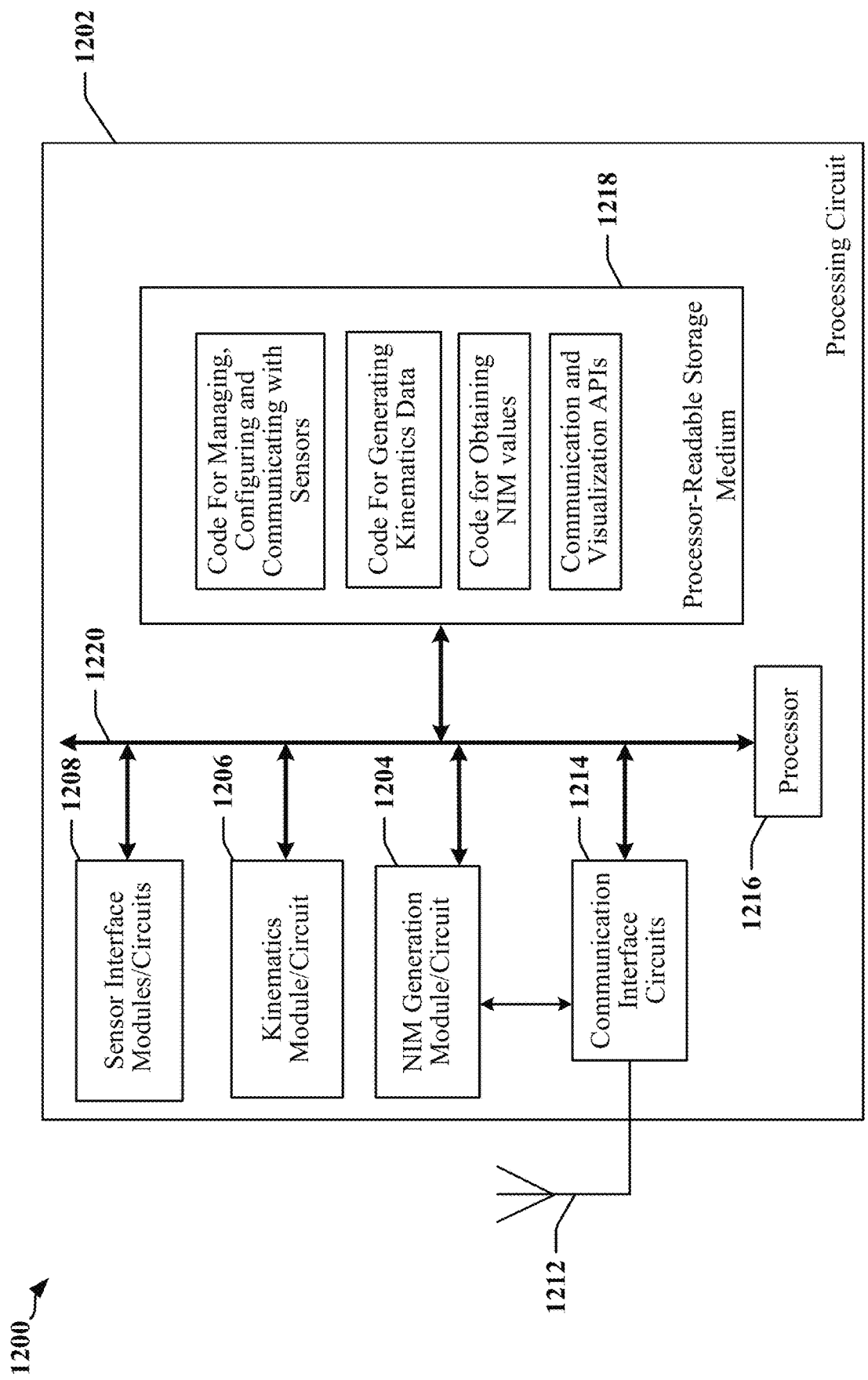
FIG. 12 illustrates an apparatus configured in accordance with certain aspects disclosed herein to implement the method illustrated in FIG. 11.

FIG. 12 is a diagram illustrating a simplified example of a hardware implementation for an apparatus 1200 employing a processing circuit 1202 configured to implement the processes described by the flowchart 1100 of FIG. 11. The processing circuit 1202 typically has a controller or processor 1216 that may include one or more microprocessors, microcontrollers, digital signal processors, sequencers and/or state machines. The processing circuit 1202 may be implemented with a bus architecture, represented generally by the bus 1220. The bus 1220 may include any number of interconnecting buses and bridges depending on the specific application of the processing circuit 1202 and overall design constraints. The bus 1220 links together various circuits including one or more processors and/or hardware modules as represented by the controller or processor 1216, the modules or circuits 1204, 1206 and 1208, and the computer-readable storage medium 1218. The apparatus 1200 may be coupled to a network using a communication interface circuit 1214. In some instances, the apparatus may communicate through one or more antennae 1212. The communication interface circuit 1214 may operate a wireless or wired communication link in accordance with a standards-defined or proprietary protocol. The bus 1220 may also link various other circuits such as timing sources, peripherals, voltage regulators, and power management circuits, which are well known in the art, and therefore, will not be described any further.

The processor 1216 is responsible for general processing, including the execution of software, code and/or instructions stored on the computer-readable storage medium 1218. The computer-readable storage medium may include a non-transitory storage medium. The software, when executed by the processor 1216, causes the processing circuit 1202 to perform one or more of the various functions described supra. The computer-readable storage medium 1218 may be used for storing data that is manipulated or used by the processor 1216 when executing software. In one example, the computer-readable storage medium 1218 stores Kinematics data, dose-response characteristics and other model-derived information. The processing circuit 1202 further includes at least one of the modules 1204, 1206 and 1208. The modules 1204, 1206 and 1208 may be software modules running in the processor 1216, resident/stored in the computer-readable storage medium 1218, one or more hardware modules coupled to the processor 1216, or some combination thereof. The modules 1204, 1206 and 1208 may include microcontroller instructions, state machine configuration parameters, or some combination thereof.

In one configuration, the apparatus 1200 includes modules and/or circuits 1208 configured to obtain, capture and/or read sensor data representative of external head motion data. The apparatus 1200 may include modules and/or circuits 1206 configured to relate external head motion data to internal strain effects, including estimates of corpus callosum strain. The apparatus 1200 may include modules and/or circuits 1204 configured to determine a NIM value from the estimate of corpus callosum strain, where the NIM value can be used to obtain a probability that the subject has been concussed by a traumatic event related to the external head motion data.

In one example, the storage medium 1218 of the apparatus 1200 maintains one or more transforms derived from a mechanistic model of head kinematics. The processing circuit 1202 may be configured to receive motion data related to an extraordinary head acceleration event from a plurality of sensors configured to detect head motion of a subject, use one or more of the transforms to determine strain at nodes of Ranvier in one or more components of the subject's brain resulting from the head acceleration event, estimate axon signal dysfunction affecting the one or more components of the subject's brain by translating the strain at the nodes of Ranvier to functional decrement of axon signaling, determine a NIM from estimated axon signal dysfunction, and generate a probability that the subject has been concussed by the head acceleration event based on the NIM.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A method implemented at a portable communication device, comprising:
   receiving motion data related to an extraordinary head acceleration event from a plurality of sensors configured to detect head motion of a subject;
   using the motion data to obtain an estimate of axon signal dysfunction affecting one or more components of the subject's brain as a result of the head acceleration event;
   determining a Neurologic Injury Measure (NIM) from the estimate of axon signal dysfunction; and
   generating a probability that the subject has been concussed by the head acceleration event based on the NIM,
   wherein the estimate of axon signal dysfunction is obtained by:
      determining strain at nodes of Ranvier in the one or more components of the subject's brain; and
      estimating axon signal dysfunction by translating the strain at the nodes of Ranvier to functional decrement of axon signaling.

2. The method of claim 1, wherein determining the strain at the nodes of Ranvier comprises:
   determining strain at nodes of Ranvier in the subject's corpus callosum.

3. The method of claim 1, further comprising:
   determining the NIM using a volume-weighted average of axon signal dysfunction over a plurality of axons in the one or more components of the subject's brain.

4. The method of claim 3, wherein the plurality of axons is located in a corpus callosum of the subject's brain.

5. The method of claim 1, wherein the head acceleration event results from an impact to the subject's head or exposure of the subject's head to a blast.

6. The method of claim 1, wherein the head acceleration event results from an application of an accelerative load to the subject's body.

7. The method of claim 1, further comprising:
   transforming the motion data to obtain head kinematics abstracted from placement of the plurality of sensors with respect to the subject's head.

8. The method of claim 7, wherein at least one sensor in the plurality of sensors is mechanically decoupled from the subject's head.

9. The method of claim 7, wherein one or more sensors in the plurality of sensors provides a stream of image data that captures movement of the subject's head.

10. The method of claim 7, further comprising:
determining a probability that the subject has been concussed using dose-response information obtained from a mechanistic concussion model.

11. The method of claim 10, wherein the dose-response information indicates a cumulative effect of multiple extraordinary head acceleration events affecting the subject's head.

12. The method of claim 7, further comprising:
correlating the NIM to an injury outcome using dose-response information obtained from a mechanistic concussion model.

13. The method of claim 7, further comprising:
correlating the NIM to an injury outcome using a fast concussion model comprising a plurality of transforms received from a network server that maintains a mechanistic concussion model.

14. The method of claim 13, further comprising:
transmitting the motion data related to the extraordinary head acceleration event to the network server that maintains the mechanistic concussion model, wherein information obtained from a plurality of extraordinary head acceleration events affecting one or more subjects is used to update the fast concussion model; and
receiving one or more updated transforms from the network server that maintains the mechanistic concussion model after the fast concussion model is updated.

15. The method of claim 13, further comprising:
receiving visualization data from the network server that maintains the mechanistic concussion model; and
providing a visualization of the extraordinary head acceleration event on the portable communication device.

16. The method of claim 7, further comprising:
configuring the plurality of sensors based on format and timing requirements defined for an interface that transforms the motion data.

17. The method of claim 16, further comprising:
generating visualization data using the motion data related to the extraordinary head acceleration event and based on configuration of the plurality of sensors; and
providing a visualization of the extraordinary head acceleration event on the portable communication device.

18. The method of claim 1, further comprising:
communicating with the plurality of sensors periodically using a wireless communication protocol, wherein the motion data related to the extraordinary head acceleration event is received during one or more periodic communication events.

19. The method of claim 1, further comprising:
receiving the motion data related to the extraordinary head acceleration event while communicating with the plurality of sensors responsive to an indication that the extraordinary head acceleration event has occurred.

20. The method of claim 1, further comprising:
alerting a user of the portable communication device when the probability that the subject has been concussed by the extraordinary head acceleration event exceeds a configured threshold.

21. An apparatus, comprising:
a communication interface adapted to couple the apparatus to a plurality of wearable sensors;
a storage medium configured with transforms generated from a mechanistic model of head kinematics; and
a processing circuit configured to:
receive motion data related to an extraordinary head acceleration event from one or more of the plurality of wearable sensors that are configured to detect head motion of a subject;
use the motion data to obtain an estimate of axon signal dysfunction affecting one or more components of the subject's brain as a result of the head acceleration event;
wherein the estimate of axon signal dysfunction is obtained by:
determining strain at nodes of Ranvier in one or more components of the subject's brain resulting from the head acceleration event; and
estimating axon signal dysfunction affecting the one or more components of the subject's brain by translating the strain at the nodes of Ranvier to functional decrement of axon signaling;
determine a Neurologic Injury Measure (NIM) from estimated axon signal dysfunction; and
generate a probability that the subject has been concussed by the head acceleration event based on the NIM.

22. A non-transitory computer readable storage medium comprising instructions that, when executed by one or more processors, causes the one or more processors to:
receive motion data related to an extraordinary head acceleration event from a plurality of sensors configured to detect head motion of a subject;
use the motion data to obtain an estimate of axon signal dysfunction affecting one or more components of the subject's brain as a result of the head acceleration event by:
determining strain at nodes of Ranvier in one or more components of the subject's brain resulting from the head acceleration event; and
estimating axon signal dysfunction affecting the one or more components of the subject's brain by translating the strain at the nodes of Ranvier to functional decrement of axon signaling;
determine a Neurologic Injury Measure (NIM) from estimated axon signal dysfunction; and
generate a probability that the subject has been concussed by the head acceleration event based on the NIM.

* * * * *